(12) United States Patent
Ackermann et al.

(10) Patent No.: US 8,470,843 B2
(45) Date of Patent: *Jun. 25, 2013

(54) AZACYCLIC COMPOUNDS

(75) Inventors: Jean Ackermann, Riehen (CH); Aurelia Conte, Basel (CH); Daniel Hunziker, Moehlin (CH); Werner Neidhart, Hagenthal-le-Bas (FR); Matthias Nettekoven, Grenzach-Wyhlen (DE); Tanja Schulz-Gasch, Ziefen (CH); Stanley Wertheimer, Croton, NY (US)

(73) Assignee: Hoffmann-La Roche Inc., Nutley, NJ (US)

( * ) Notice: Subject to any disclaimer, the term of this patent is extended or adjusted under 35 U.S.C. 154(b) by 35 days.

This patent is subject to a terminal disclaimer.

(21) Appl. No.: 13/180,582

(22) Filed: Jul. 12, 2011

(65) Prior Publication Data

US 2012/0015970 A1 Jan. 19, 2012

(30) Foreign Application Priority Data

Jul. 13, 2010 (EP) .................... 10169352

(51) Int. Cl.
  *A61K 31/438* (2006.01)
  *C07D 221/20* (2006.01)
  *C07D 471/10* (2006.01)
(52) U.S. Cl.
  USPC ............................ 514/278; 546/16

(58) Field of Classification Search
  USPC .............................. 546/16; 514/278
  See application file for complete search history.

(56) References Cited

FOREIGN PATENT DOCUMENTS

JP 2001/261679 9/2001
WO 2007/067504 6/2007

OTHER PUBLICATIONS

Suess et al., "Helvetica Chimica Acta" 60(5):1650-1656 (1977).
PCT International Search Report—PCT/EP2011/061579—Mailed Aug. 16, 2011.
English language Abstract of JP2001/261679.

*Primary Examiner* — Rita Desai

(57) ABSTRACT

The invention provides novel compounds having the general formula (I)

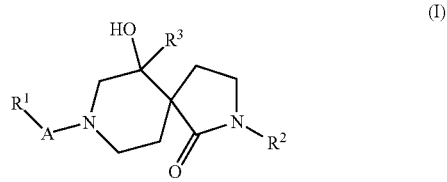

wherein $R^1$, $R^2$, $R^3$ and A are as described herein, compositions including the compounds and methods of using the compounds.

6 Claims, No Drawings

AZACYCLIC COMPOUNDS

PRIORITY TO RELATED APPLICATION(S)

This application claims the benefit of European Patent Application No. 10169352.1, filed Jul. 13, 2010, which is hereby incorporated by reference in its entirety.

FIELD OF THE INVENTION

The present invention relates to organic compounds useful for therapy or prophylaxis in a mammal, and in particular to inhibitors of hormone sensitive lipase (HSL) for the treatment of diabetes, metabolic syndrome and obesity.

SUMMARY OF THE INVENTION

The present invention provides novel compounds of formula (I)

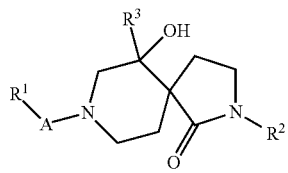

wherein
$R^1$ is selected from the group consisting of alkyl, cycloalkyl, alkylcycloalkyl, cycloalkylalkyl, alkylcycloalkylalkyl, haloalkyl, amino, aminoalkyl, piperidinyl, piperazinyl, morpholinyl, imidazolyl, pyrazolyl, triazolyl, tetrazolyl, oxazolyl, isoxazolyl, thiazolyl, phenyl, pyridinyl, pyrazinyl, pyrimidyl and pyridazinyl,
wherein said piperidinyl, piperazinyl, morpholinyl, imidazolyl, pyrazolyl, triazolyl, tetrazolyl, oxazolyl, isoxazolyl, thiazolyl, phenyl, pyridinyl, pyrazinyl, pyrimidyl and pyridazinyl are optionally substituted with one to three substituents independently selected from the group consisting of alkyl, cycloalkyl, alkylcycloalkyl, cycloalkylalkyl, alkylcycloalkylalkyl, halogen, haloalkyl, hydroxy, hydroxyalkyl, alkoxy, alkoxyalkyl, haloalkoxy and hydroxyhaloalkyl, and wherein said amino and aminoalkyl are optionally substituted on the nitrogen atom with one to two substituents independently selected from the group consisting of alkyl, cycloalkyl, alkylcycloalkyl, cycloalkylalkyl, alkylcycloalkylalkyl, hydroxyalkyl and alkoxyalkyl;
$R^2$ is selected from the group consisting of phenyl, pyridinyl, pyrazinyl, pyrimidyl and pyridazinyl,
wherein said phenyl, pyridinyl, pyrazinyl, pyrimidyl and pyridazinyl are substituted with one to three substituents independently selected from the group consisting of alkyl, cycloalkyl, alkylcycloalkyl, cycloalkylalkyl, alkylcycloalkylalkyl, halogen, haloalkyl, hydroxy, hydroxyalkyl, alkoxy, alkoxyalkyl, haloalkoxy and hydroxyhaloalkyl;
$R^3$ is selected from the group consisting of hydrogen, alkyl, cycloalkyl and haloalkyl;
A is selected from the group consisting of —$(CH_2)_n$—, —C(O)— and —S(O)$_2$—; and
n is zero, 1 or 2.

The present invention also provides pharmaceutically acceptable salts and esters of the aforementioned compounds.

Further objects of the present invention relate to the use of compounds of formula (I) and their aforementioned salts and esters as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of illnesses, especially in the treatment or prophylaxis of diabetes, metabolic syndrome, dyslipidemia, atherosclerosis, obesity, cardiovascular diseases, myocardial dysfunction, inflammation, nonalkoholic fatty liver disease or nonalkoholic steatohepatitis and the use of the said compounds, salts or esters for the production of medicaments for the treatment or prophylaxis of diabetes, metabolic syndrome, dyslipidemia, atherosclerosis, obesity, cardiovascular diseases, myocardial dysfunction, inflammation, nonalkoholic fatty liver disease or nonalkoholic steatohepatitis.

BACKGROUND OF THE INVENTION

The main physiological role of white adipose tissue (WAT) is to supply energy when it is needed by other tissues. In mammals, white adipose tissue is the primary energy storage depot, accumulating fuel reserves in the form of triacylglycerol (TAG) during times of energy excess. The release of free fatty acids (FFA) from TAG is stimulated by catecholamines and regulated by hormones such as insulin, glucagon and epinephrine. The most important enzyme in WAT believed responsible for hormone regulated hydrolysis of triglyceride is hormone sensitive lipase (HSL).

Dysregulation of adipocyte lipolysis, resulting in elevated circulating non-esterified fatty acids (NEFA) is associated with obesity and co-morbidities including the development of type 2 diabetes. Obese or insulin resistant subjects have increased visceral adipose tissue depots. These depots contain elevated levels of HSL protein and exhibit enhanced lipolytic activity as they are resistant to the insulin-mediated suppression of lipolysis. This results in increased plasma levels of free fatty acids (FFA), which further exacerbates insulin resistance due to the accumulation of triglycerides in tissues other than WAT such as liver, pancreas and muscle. Thus, the elevated plasma levels of FFA due to increased HSL activity contributes to and worsens insulin resistance in obese and type 2 diabetic individuals. Restoring the exaggerated plasma FFA and triglyceride levels through inhibition of HSL would reduce the accumulation of triglycerides in tissues other than WAT, such as liver, muscle and the pancreas resulting in decreased hepatic glucose output, increased muscle fatty acid oxidation and improving β-cell function.

Elevated FFAs are also associated with increased cardiovascular risk, including atherosclerosis and myocardial dysfunction. Furthermore high lipolytic activity and elevated FFAs lead to increased insulin resistance and hypertension in hypertensive rats. The FFA collect in the liver and lead to increased production of TAG, which are packaged into very low density lipoproteins (VLDL) which are secreted. Therefore, reducing the activity of HSL would decrease the release of FFA to the blood, thus limiting the supply of FFA to the liver for TAG synthesis. Thus, HSL inhibitors could have beneficial effects as treatment of nonalkoholic fatty liver disease (NAFLD) and nonalkoholic steatohepatitis (NASH).

DETAILED DESCRIPTION OF THE INVENTION

The present invention provides novel compounds of formula (I)

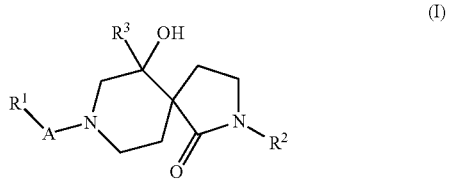

wherein
R¹ is selected from the group consisting of alkyl, cycloalkyl, alkylcycloalkyl, cycloalkylalkyl, alkylcycloalkylalkyl, haloalkyl, amino, aminoalkyl, piperidinyl, piperazinyl, morpholinyl, imidazolyl, pyrazolyl, triazolyl, tetrazolyl, oxazolyl, isoxazolyl, thiazolyl, phenyl, pyridinyl, pyrazinyl, pyrimidyl and pyridazinyl, wherein said piperidinyl, piperazinyl, morpholinyl, imidazolyl, pyrazolyl, triazolyl, tetrazolyl, oxazolyl, isoxazolyl, thiazolyl, phenyl, pyridinyl, pyrazinyl, pyrimidyl and pyridazinyl are optionally substituted with one to three substituents independently selected from the group consisting of alkyl, cycloalkyl, alkylcycloalkyl, cycloalkylalkyl, alkylcycloalkylalkyl, halogen, haloalkyl, hydroxy, hydroxyalkyl, alkoxy, alkoxyalkyl, haloalkoxy and hydroxyhaloalkyl, and wherein said amino and aminoalkyl are optionally substituted on the nitrogen atom with one to two substituents independently selected from the group consisting of alkyl, cycloalkyl, alkylcycloalkyl, cycloalkylalkyl, alkylcycloalkylalkyl, hydroxyalkyl and alkoxyalkyl;

R² is selected from the group consisting of phenyl, pyridinyl, pyrazinyl, pyrimidyl and pyridazinyl, wherein said phenyl, pyridinyl, pyrazinyl, pyrimidyl and pyridazinyl are substituted with one to three substituents independently selected from the group consisting of alkyl, cycloalkyl, alkylcycloalkyl, cycloalkylalkyl, alkylcycloalkylalkyl, halogen, haloalkyl, hydroxy, hydroxyalkyl, alkoxy, alkoxyalkyl, haloalkoxy and hydroxyhaloalkyl;

R³ is selected from the group consisting of hydrogen, alkyl, cycloalkyl and haloalkyl;

A is selected from the group consisting of —(CH$_2$)$_n$—, —C(O)— and —S(O)$_2$—; and n is zero, 1 or 2.

The present invention also provides pharmaceutically acceptable salts and esters of the aforementioned compounds.

The term "alkyl", alone or in combination, signifies a straight-chain or branched-chain alkyl with 1 to 8 carbon atoms, in particular with 1 to 6 carbon atoms and further particular with 1 to 4 carbon atoms. Examples are methyl, ethyl, propyl, isopropyl, n-butyl, isobutyl, tert-butyl, n-pentyl, methylbutyl, dimethylpropyl, ethylpropyl, n-hexyl, methylpentyl, dimethylbutyl, trimethylpropyl and ethylmethylpropyl. Particular examples are methyl, ethyl, propyl, isopropyl, butyl, isobutyl and dimethylpropyl.

The term "cycloalkyl", alone or in combination, signifies a cycloalkyl ring with 3 to 8 carbon atoms and in particular with 3 to 6 carbon atoms. Examples are cyclopropyl, cyclobutyl, cyclopentyl, cyclohexyl, cycloheptyl and cyclooctyl. A particular example is cyclopropyl.

The term "alkylcycloalkyl", alone or in combination, signifies a cycloalkyl, wherein one or more hydrogen atoms are replaced by an alkyl. Examples are methyl-cyclopropyl, dimethyl-cyclopropyl, methyl-cyclobutyl, dimethyl-cyclobutyl, methyl-cyclopentyl, dimethyl-cyclopentyl, methyl-cyclohexyl and dimethyl-cyclohexyl. Particular examples are methyl-cyclopropyl and dimethyl-cyclopropyl.

The term "cycloalkylalkyl", alone or in combination, signifies an alkyl, wherein one or more hydrogen atoms are replaced by a cycloalkyl. Examples are cyclopropylmethyl, cyclopropylethyl, cyclobutylmethyl, cyclobutylethyl, cyclopentylmethyl, cyclopentylethyl, cyclohexylmethyl, cyclohexylethyl, cycloheptylmethyl, cycloheptylethyl, cyclooctylmethyl and cyclooctylethyl. Particular examples are cyclopropylmethyl, cyclopropylethyl, cyclobutylmethyl and cyclobutylethyl.

The term "alkylcycloalkylalkyl", alone or in combination, signifies an alkyl, wherein one or more hydrogen atoms are replaced by an alkylcycloalkyl. Examples are methyl-cyclopropylmethyl, dimethyl-cyclopropylmethyl, methyl-cyclopropylethyl, dimethyl-cyclopropylethyl, methyl-cyclobutylmethyl, dimethyl-cyclobutylmethyl, methyl-cyclobutylethyl, dimethyl-cyclobutylethyl, methyl-cylopentylmethyl, dimethyl-cylopentylmethyl, methyl-cyclopentylethyl, dimethyl-cyclopentylethyl, methyl-cyclohexylmethyl, dimethyl-cyclohexylmethyl, methyl-cyclohexylethyl, dimethyl-cyclohexylethyl, methyl-cycloheptylmethyl, dimethyl-cycloheptylmethyl, methyl-cycloheptylethyl, dimethyl-cycloheptylethyl, methyl-cyclooctylmethyl, dimethyl-cyclooctylmethyl, methyl-cyclooctylethyl and dimethyl-cyclooctylethyl.

The term "hydroxy", alone or in combination, signifies the —OH group.

The term "hydroxyalkyl", alone or in combination, signifies an alkyl as defined before, wherein one or more hydrogen atoms are replaced by a hydroxy. Examples of hydroxyalkyl are hydroxymethyl, hydroxyethyl, hydroxypropyl, hydroxymethylpropyl and dihydroxypropyl. Particular examples are hydroxyethyl and hydroxymethylpropyl.

The term "alkoxy", alone or in combination, signifies a group of the formula —O-alkyl in which the term alkyl has the previously given significance. Examples are methoxy, ethoxy, n-propoxy, isopropoxy, n-butoxy, isobutoxy, sec-butoxy and tert-butoxy.

The term "alkoxyalkyl", alone or in combination, signifies an alkyl as defined before, wherein one or more hydrogen atoms are replaced by an alkoxy. Examples of methoxymethyl, ethoxymethyl, methoxymethyl, ethoxyethyl, methoxypropyl and ethoxypropyl.

The terms "halogen" and "halo", alone or in combination, signify fluorine, chlorine, bromine or iodine. Particular examples are fluorine or chlorine.

The term "haloalkyl", alone or in combination, signifies an alkyl as defined before, wherein one or more hydrogen atoms are replaced by a halogen. Examples of haloalkyl are fluoromethyl, difluoromethyl, trifluoromethyl, trifluoroethyl, trifluoromethylethyl or pentafluoroethyl. A particular example is trifluoroethyl.

The term "haloalkoxy", alone or in combination, signifies an alkoxy as defined before, wherein one or more hydrogen atoms are replaced by a halogen. Examples of haloalkoxy are fluoromethoxy, difluoromethoxy, trifluoromethoxy, trifluoroethoxy, trifluoromethylethoxy, trifluorodimethylethoxy, or pentafluoroethoxy. Particular examples are trifluoromethoxy and trifluoromethylethoxy.

The term "hydroxyhaloalkyl", alone or in combination, signifies an alkyl as defined before, wherein one or more hydrogen atoms of the alkyl are replaced by a hydroxy and wherein one or more hydrogen atoms of the alkyl are replaced by a halogen, in which the terms hydroxy and halogen have the previously given significances. Examples of hydroxyhaloalkyl are hydroxytrifluoroethyl, hydroxytrifluoropropyl, hydroxyhexafluoropropyl.

The term "amino" alone signifies the —NH$_2$ group.

The term "aminoalkyl", alone or in combination, signifies an alkyl as defined before, wherein one or more hydrogen atoms are replaced by an amino. Examples of aminoalkyl are aminomethyl, aminoethyl, aminopropyl and aminomethylpropyl. Particular examples are aminoethyl and aminopropyl.

The term "carbonyl", alone or in combination, signifies the —C(O)— group.

The term "sulfonyl", alone or in combination, signifies the —S(O)$_2$— group.

The term "protecting group" refers to groups which are used to block the reactivity of functional groups such as amino groups or hydroxy groups. Examples of protecting groups are tert-butoxycarbonyl (Boc), benzyloxycarbonyl (Cbz), fluorenylmethoxycarbonyl (Fmoc) or benzyl (Bn). A particular protecting group is tert-butoxycarbonyl (Boc).

Cleavage of protecting groups can be done using standard methods known by the man skilled in the art such as hydrogenation or in the presence of an acid, e.g. HCl or TFA, or a base, e.g. triethylamine.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

The compounds of formula (I) can also be solvated, e.g. hydrated. The solvation can be effected in the course of the manufacturing process or can take place e.g. as a consequence of hygroscopic properties of an initially anhydrous compound of formula (I) (hydration). The term pharmaceutically acceptable salts also includes physiologically acceptable solvates.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

An embodiment of the present invention relates to compounds according to formula (I) as described above.

Another embodiment of the present invention relates to pharmaceutically acceptable salts of compounds according to formula (I) as described above.

A further embodiment of the present invention are compounds according to formula (I) as described above, wherein $R^1$ is selected from the group consisting of alkyl, cycloalkyl, haloalkyl, pyrazolyl, phenyl and pyridinyl, wherein said pyrazolyl, phenyl and pyridinyl are optionally substituted with one to three substituents independently selected from the group consisting of alkyl, cycloalkyl, cycloalkylalkyl, halogen, haloalkyl, hydroxy, hydroxyalkyl, alkoxy, alkoxyalkyl, haloalkoxy and hydroxyhaloalkyl.

A particular embodiment of the present invention are compounds according to formula (I) as described above, wherein $R^1$ is selected from the group consisting of alkyl, cycloalkyl, haloalkyl, pyrazolyl, phenyl and pyridinyl, wherein said pyrazolyl, phenyl and pyridinyl are optionally substituted with one to three substituents independently selected from the group consisting of alkyl, halogen and haloalkoxy.

A particular embodiment of the present invention are compounds according to formula (I) as described above, wherein $R^1$ is selected from the group consisting of alkyl, cycloalkyl, haloalkyl, phenyl, substituted pyrazolyl, substituted phenyl and substituted pyridinyl, wherein said substituted pyrazolyl, substituted phenyl and substituted pyridinyl are substituted with one to three substituents independently selected from the group consisting of alkyl, halogen and haloalkoxy.

Also a particular embodiment of the present invention are compounds according to formula (I) as described above, wherein $R^1$ is selected from the group consisting of alkyl, pyrazolyl substituted with one alkyl and phenyl substituted with one halogen.

A particular embodiment of the present invention are compounds according to formula (I) as described above, wherein $R^1$ is selected from the group consisting of 2,2-dimethylpropyl, 1-methyl-1H-pyrazol-5-yl and chlorophenyl.

In a further embodiment of the present invention are compounds according to formula (I) as described above, wherein $R^2$ is phenyl or pyridinyl, wherein said phenyl and pyridinyl are optionally substituted with one to three substituents independently selected from the group consisting of alkyl, cycloalkyl, cycloalkylalkyl, halogen, haloalkyl, hydroxy, hydroxyalkyl, alkoxy, alkoxyalkyl, haloalkoxy and hydroxyhaloalkyl.

In a particular embodiment of the present invention are compounds according to formula (I) as described above, wherein $R^2$ is phenyl substituted with one to three substituents independently selected from haloalkyl and haloalkoxy.

The present invention also relates to compounds according to formula (I) as described above, wherein $R^2$ is selected from the group consisting of 2,2,2-trifluoroethylphenyl, trifluoromethoxyphenyl and 1,1,1-trifluoro-2-methylethoxy.

An alternative embodiment of the present invention are compounds according to formula (I) as described above, wherein $R^3$ is selected from the group consisting of hydrogen, alkyl and haloalkyl.

A particular embodiment of the present invention are compounds according to formula (I) as described above, wherein $R^3$ is hydrogen or alkyl.

A further embodiment of the present invention are compounds according to formula (I) as described above, wherein $R^3$ is hydrogen or methyl.

A particular embodiment of the present invention are compounds according to formula (I) as described above, wherein A is —C(O)—.

A further particular embodiment of the present invention are compounds according to formula (I) as described above, wherein A is —S(O)$_2$—.

An alternative embodiment of the present invention are compounds according to formula (I) as described above, wherein A is —(CH$_2$)$_n$—.

The present invention also relates to compounds according to formula (I) as described above, wherein n is 1.

Also an embodiment of the present invention are compounds according to formula (I) as described above of formula (Ia) or (Ib) and mixtures thereof.

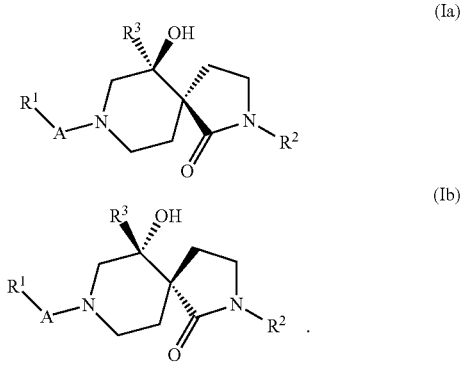

A further particular embodiment of the present invention are compounds according to formula (I) as described above of formula (Ic) or (Id) and mixtures thereof.

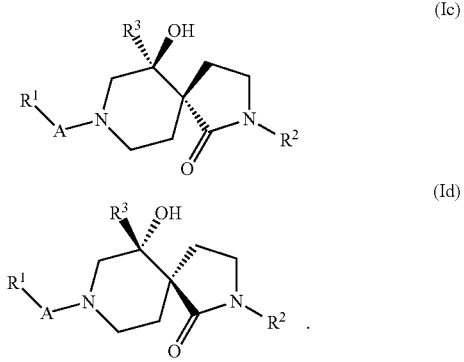

Particular examples of compounds of formula (I) as described above are selected from the group consisting of:
(5SR,6RS)-8-Benzyl-6-hydroxy-2-(4-trifluoromethoxy-phenyl)-2,8-diaza-spiro[4.5]decan-1-one;
(5RS,6RS)-8-(2-Chloro-benzenesulfonyl)-6-hydroxy-2-(4-trifluoromethoxy-phenyl)-2,8-diaza-spiro[4.5]decan-1-one;
(5RS,6RS)-8-(2-Chloro-pyridine-3-sulfonyl)-6-hydroxy-2-(4-trifluoromethoxy-phenyl)-2,8-diaza-spiro[4.5]decan-1-one;
(5RS,6RS)-6-Hydroxy-8-(2-trifluoromethoxy-benzenesulfonyl)-2-(4-trifluoromethoxy-phenyl)-2,8-diaza-spiro[4.5]decan-1-one;
(5RS,6RS)-8-Cyclopropanesulfonyl-6-hydroxy-2-(4-trifluoromethoxy-phenyl)-2,8-diaza-spiro[4.5]decan-1-one;
(5RS,6RS)-6-Hydroxy-8-(2-methyl-propane-1-sulfonyl)-2-(4-trifluoromethoxy-phenyl)-2,8-diaza-spiro[4.5]decan-1-one;
(5RS,6RS)-8-(2-Chloro-benzenesulfonyl)-6-hydroxy-2-[4-(2,2,2-trifluoro-ethyl)-phenyl]-2,8-diaza-spiro[4.5]decan-1-one;
(5RS,6RS)-6-Hydroxy-8-(2-methyl-2H-pyrazole-3-sulfonyl)-2-[4-(2,2,2-trifluoro-ethyl)-phenyl]-2,8-diaza-spiro[4.5]decan-1-one;
(5RS,6RS)-8-(2,2-Dimethyl-propane-1-sulfonyl)-6-hydroxy-2-[4-(2,2,2-trifluoro-ethyl)-phenyl]-2,8-diaza-spiro[4.5]decan-1-one;
(5RS,6RS)-8-(2-Chloro-benzenesulfonyl)-6-hydroxy-2-[4-((rac)-2,2,2-trifluoro-1-methyl-ethoxy)-phenyl]-2,8-diaza-spiro[4.5]decan-1-one;
(5RS,6RS)-6-Hydroxy-8-(2-methyl-2H-pyrazole-3-sulfonyl)-2-[4-((rac)-2,2,2-trifluoro-1-methyl-ethoxy)-phenyl]-2,8-diaza-spiro[4.5]decan-1-one;
(5RS,6RS)-8-(2-Chloro-benzenesulfonyl)-6-hydroxy-6-methyl-2-(4-trifluoromethoxy-phenyl)-2,8-diaza-spiro[4.5]decan-1-one;
(5RS,6SR)-8-(2-Chloro-benzenesulfonyl)-6-hydroxy-6-methyl-2-(4-trifluoromethoxy-phenyl)-2,8-diaza-spiro[4.5]decan-1-one; and
(5RS ,6SR)-8-(2-Chloro-benzenesulfonyl)-6-hydroxy-2-(4-trifluoromethoxy-phenyl)-2,8-diaza-spiro[4.5]decan-1-one.

Further particular examples of compounds of formula (I) as described above are selected from the group consisting of:
(5RS,6RS)-8-(2-Chloro-benzenesulfonyl)-6-hydroxy-2-[4-(2,2,2-trifluoro-ethyl)-phenyl]-2,8-diaza-spiro[4.5]decan-1-one;
(5RS,6RS)-6-Hydroxy-8-(2-methyl-2H-pyrazole-3-sulfonyl)-2-[4-(2,2,2-trifluoro-ethyl)-phenyl]-2,8-diaza-spiro[4.5]decan-1-one;
(5RS,6RS)-8-(2,2-Dimethyl-propane-1-sulfonyl)-6-hydroxy-2-[4-(2,2,2-trifluoro-ethyl)-phenyl]-2,8-diaza-spiro[4.5]decan-1-one; and
(5RS,6RS)-6-Hydroxy-8-(2-methyl-2H-pyrazole-3-sulfonyl)-2-[4-((rac)-2,2,2-trifluoro-1-methyl-ethoxy)-phenyl]-2,8-diaza-spiro[4.5]decan-1-one.

Processes for the manufacture of compounds of formula (I) as described above are an object of the invention.

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. In case a mixture of enantiomers or diastereoisomers is produced during a reaction, these enantiomers or diastereoisomers can be separated by methods described herein or known to the man skilled in the art such as e.g. chiral chromatography or crystallization. The substituents and indices used in the following description of the processes have the significance given herein.

Scheme 1 describes the synthesis of intermediates used in reactions described herein.

Scheme 1

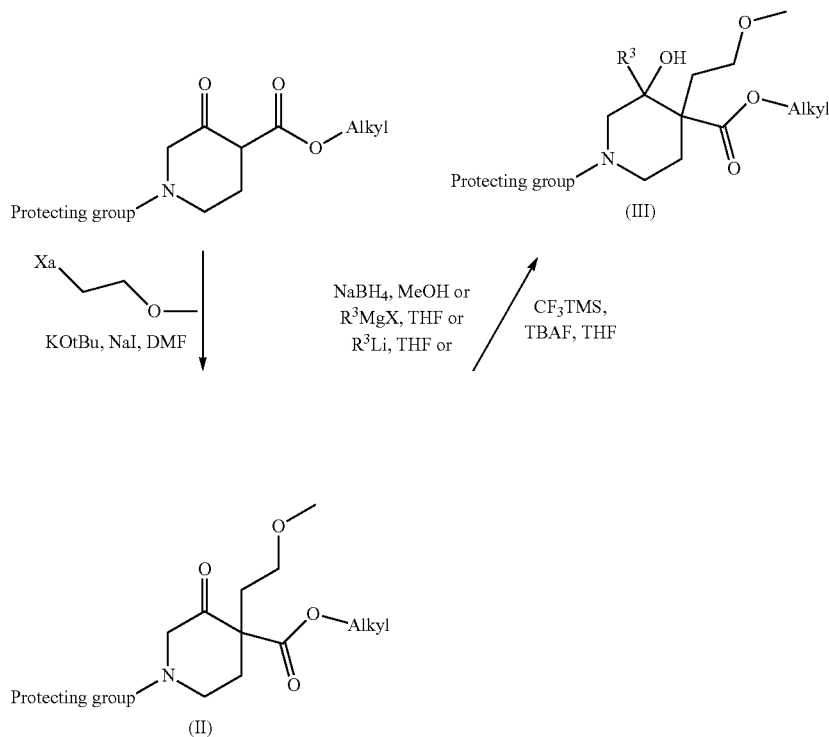

Xa is halogen, in particular Br and I
X is halogen, in particular Cl and Br
Alkyl is e.g. methyl or ethyl
Protecting group is e.g Bn Starting material such as commercially available 1-benzyl-3-oxopiperidine-4-carboxylic acid methyl ester is treated with a suitable base such as potassium tert-butoxide in an appropriate solvent such as DMF followed by the addition of 1-bromo-2-methoxyethane to give compounds of general formula (II). The compounds of general formula (II) can then either be reduced to compounds of general formula (III), wherein R3 is hydrogen using an appropriate reducing agent such as $NaBH_4$ in methanol or can be reacted with a suitable carbon nucleophiles, for example, Grignard reagents of formula $R^3MgX$, lithium derivatives of formula $R^3Li$ or zinc reagents to give compounds of formula (III), wherein $R^3$ is alkyl, cycloalkyl or haloalkyl. The reactions are carried out in appropriate solvents under conditions known to those skilled in the art.

Scheme 2

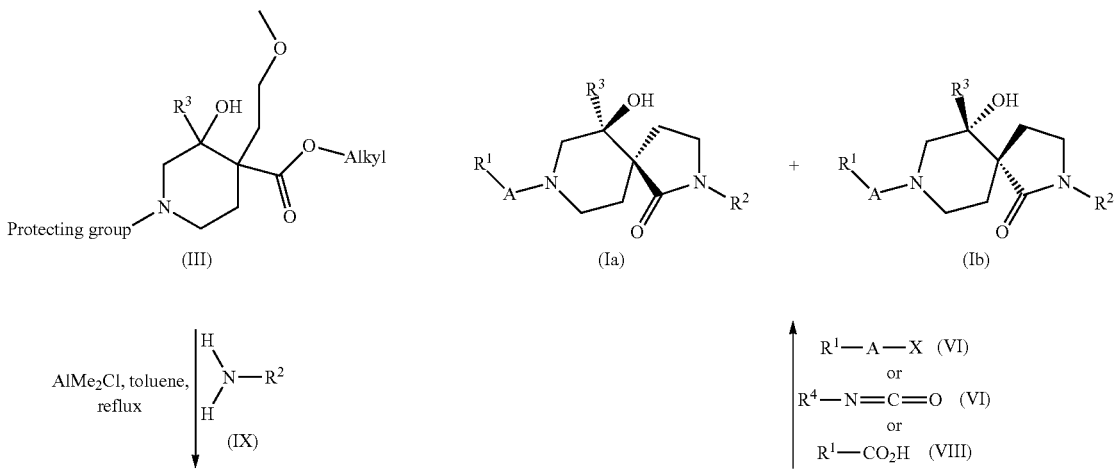

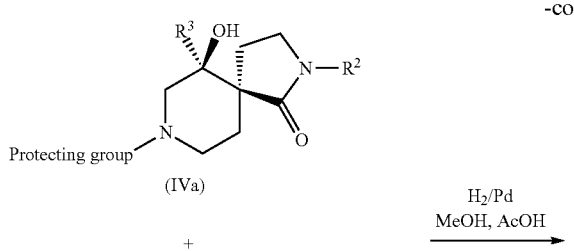

(IVa)

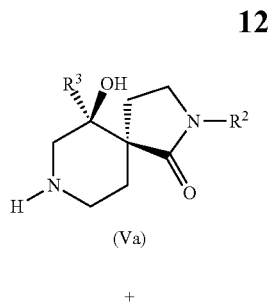

(Va)

-continued

(IVb)

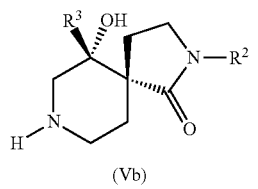

(Vb)

X is halogen, in particular Cl and Br
Alkyl is e.g. methyl or ethyl
Protecting group is e.g Bn Subsequent formation of the 2-aza-spiro[4.5]decan-1-one backbone can be achieved as outlined in Scheme 2, by treatment of compounds of general formula (III) with a compound of general formula (IX) and dimethylaluminium chloride in a solvent such as toluene at reflux temperature to give compounds of general formula (IVa), (IVb) or mixtures thereof. Alternatively, dioxane can be used as solvent and trimethylaluminium as the organometallic reagent. Deprotection by standard hydrogenation conditions gives compounds of general formula (Va), (Vb) or mixtures thereof. Subsequent reaction with compounds of general formula (VI) in an appropriate solvent such as THF, methylene chloride, DMF or similar in the presence of a base such as sodium hydride, pyridine, triethylamine or DMAP yields compounds of general formula (Ia), (Ib) or mixtures thereof. Compounds of general formula (Ia), (Ib) or mixtures thereof, wherein A is —C(O)— and $R^1$ is amino or amino substituted on the nitrogen atom with one substituent selected from alkyl, cycloalkyl, alkylcycloalkyl, cycloalkylalkyl, alkylcycloalkylalkyl, hydroxyalkyl and alkoxyalkyl, can be prepared from compounds of general formula (Va), (Vb) or mixtures thereof and from compounds of general formula (VII), wherein $R^4$ is alkyl, cycloalkyl, alkylcycloalkyl, cycloalkylalkyl, alkylcycloalkylalkyl, hydroxyalkyl or alkoxyalkyl. Compounds of general formula (VIII) can be used in the reaction together with an appropriate condensation reagent such as the EDC, BOP and the like in solvents such as THF, acetonitrile and a base e.g. Hunigs's base or triethylamine or DMAP to give the compounds of general formula (Ia), (Ib) or mixtures thereof, wherein A is —C(O)—.

An alternative sequence to prepare compounds of general formula (I) is outlined in scheme 3. Compounds of general formula (I), wherein $R^3$ is H can be oxidized with various oxidizing agents such as oxalyl chloride/DMSO/amine base, TEMPO/NaOCl or many other oxidizing agents under appropriate conditions to give compounds of general formula (X). The subsequent conversion of compounds of general formula (X) to compounds of general formula (I) can be achieved similarly as described above.

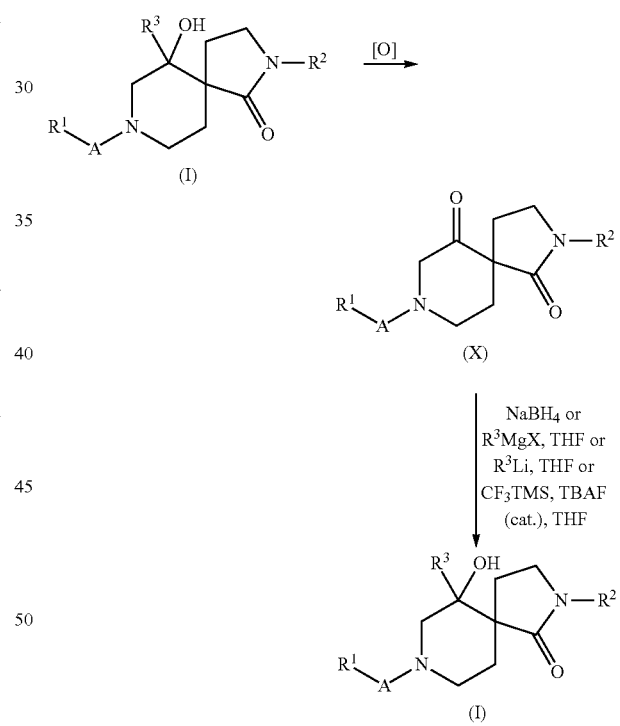

Also an embodiment of the present invention is a process to prepare a compound of formula (I) as defined above

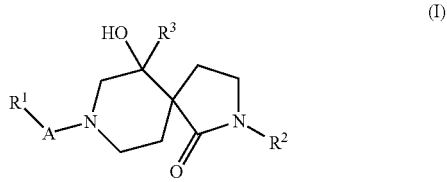

comprising the reaction of
a) a compound of formula (V) in the presence of a compound of formula (VI);

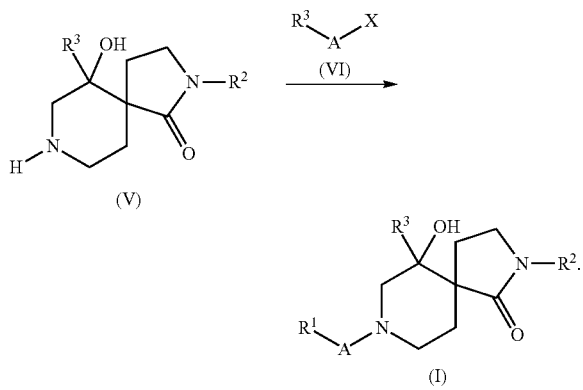

In particular in the presence of a base, particularly sodium hydride in case A is —(CH$_2$)$_n$—, and pyridine in case A is —C(O)— or —S(O)$_2$—, in a solvent, particularly THF in case A is —(CH$_2$)$_n$—, and in pyridine in case A is —C(O)— or —S(O)$_2$—, at a temperature comprised between −78° C. and RT, wherein R$^1$, R$^2$, R$^3$ and A are as defined above and X is halogen, particularly chlorine in case A is —C(O)— or —S(O)$_2$—, and iodine or bromine in case A is —(CH$_2$)$_n$—;
b) a compound of formula (V) in the presence of a compound of formula (VII);

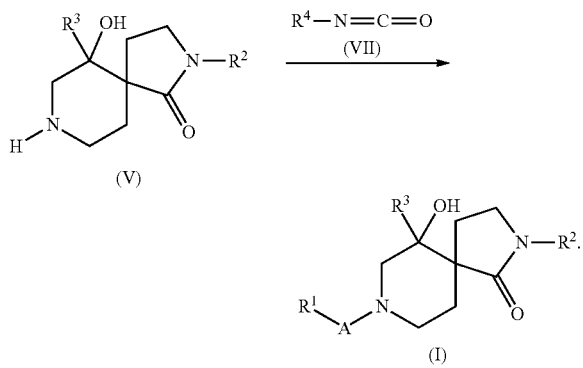

In particular in the presence of a base, particularly Hunig's base or triethylamine, in a solvent, particularly THF or DMF, at a temperature comprised between RT and 160° C., wherein R$^2$, R$^3$ and R$^4$ are as defined above and R$^1$ is amino or aminoalkyl substituted on the nitrogen atom with one substituent selected from alkyl, cycloalkyl, alkylcycloalkyl, cycloalkylalkyl, alkylcycloalkylalkyl, hydroxyalkyl and alkoxyalkyl and A is —C(O)—;
or
c) a compound of formula (V) in the presence of a compound of formula (VIII);

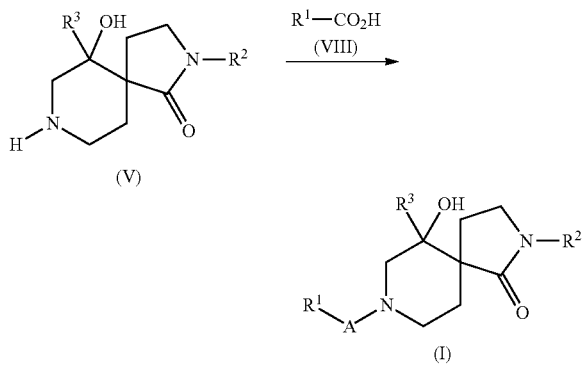

In particular in the presence of a condensation reagent, particularly EDC or BOP, and a base, particularly DMAP or triethylamine, in a solvent, particularly THF or acetonitrile, wherein R$^1$, R$^2$ and R$^3$ and A are as defined above and A is —C(O)—.

Particular intermediates are selected from
1-Benzyl-4-(2-methoxy-ethyl)-3-oxo-piperidine-4-carboxylic acid ethyl ester;
1-Benzyl-3-hydroxy-4-(2-methoxy-ethyl)-piperidine-4-carboxylic acid ethyl ester;
(5SR,6RS)-6-Hydroxy-2-(4-trifluoromethoxy-phenyl)-2,8-diaza-spiro[4.5]decan-1-one;
(5SR,6RS)-8-Benzyl-6-hydroxy-2-[4-(2,2,2-trifluoro-ethyl)-phenyl]-2,8-diaza-spiro[4.5]decan-1-one;
(5SR,6RS)-6-Hydroxy-2-[4-(2,2,2-trifluoro-ethyl)-phenyl]-2,8-diaza-spiro[4.5]decan-1-one;
(5SR,6RS)-8-Benzyl-6-hydroxy-2-[-4-((rac)-2,2,2-trifluoro-1-methyl-ethoxy)-phenyl]-2,8-diaza-spiro[4.5]decan-1-one;
(5SR,6RS)-6-Hydroxy-2-[4-((rac)-2,2,2-trifluoro-1-methyl-ethoxy)-phenyl]-2,8-diaza-spiro[4.5]decan-1-one; and
1-Benzyl-3-hydroxy-4-(2-methoxy-ethyl)-3-trifluoromethyl-piperidine-4-carboxylic acid ethyl ester.

A further object of the present invention comprises a compound according to formula (I) as described above, when manufactured according to any one of the described processes.

Also an object of the present invention are compounds according to formula (I) as described above for use as therapeutically active substance.

Likewise an object of the present invention are pharmaceutical compositions comprising a compound according to formula (I) as described above and a therapeutically inert carrier.

Also an object of the present invention are compounds according to formula (I) as described above for the preparation of a medicament for the treatment or prophylaxis of illnesses which are caused by disorders associated e.g. with the enzyme hormone-sensitive lipase.

A particular embodiment of the present invention are compounds according to formula (I) as described above for the preparation of a medicament for the treatment or prophylaxis of diabetes, metabolic syndrome, dyslipidemia, atherosclerosis or obesity.

Also a particular embodiment of the present invention are compounds according to formula (I) as described above for the preparation of a medicament for the treatment or prophylaxis of cardiovascular diseases, myocardial dysfunction, inflammation, nonalkoholic fatty liver disease or nonalkoholic steatohepatitis.

A further particular embodiment of the present invention are compounds according to formula (I) as described above for the preparation of medicaments for the treatment or prophylaxis of diabetes.

Also a further particular embodiment of the present invention are compounds according to formula (I) as described above for the preparation of medicaments for the treatment or prophylaxis of diabetes Type II.

The present invention also relates to the use of a compound according to formula (I) as described above for the preparation of a medicament for the treatment or prophylaxis of diabetes, metabolic syndrome, dyslipidemia, atherosclerosis or obesity.

Also an embodiment of the present invention is the use of a compound according to formula (I) as described above for the preparation of a medicament for the treatment or prophylaxis of cardiovascular diseases, myocardial dysfunction, inflammation, nonalkoholic fatty liver disease or nonalkoholic steatohepatitis.

A particular embodiment of the present invention is the use of a compound according to formula (I) as described above for the preparation of medicaments for the treatment or prophylaxis of diabetes.

A further particular embodiment of the present invention is the use of a compound according to formula (I) as described above for the preparation of medicaments for the treatment or prophylaxis of diabetes Type II.

Also an object of the invention is a method for the treatment or prophylaxis of diabetes, metabolic syndrome, dyslipidemia, atherosclerosis or obesity, which method comprises administering an effective amount of a compound according to formula (I) as described above.

Also an embodiment of the present invention is a method for the treatment or prophylaxis of cardiovascular diseases, myocardial dysfunction, inflammation, nonalkoholic fatty liver disease or nonalkoholic steatohepatitis, which method comprises administering an effective amount of a compound according to formula (I) as described above.

A particular embodiment of the present invention is a method for the treatment or prophylaxis of diabetes, which method comprises administering an effective amount of a compound according to formula (I) as described above.

A further particular embodiment of the present invention is a method for the treatment or prophylaxis of diabetes Type II, which method comprises administering an effective amount of a compound according to formula (I) as described above.

Assay Procedures

Production of Human Full Length Hormone Sensitive Lipase-His[6]:
1) Cloning: cDNA was prepared from commercial human brain polyA+RNA and used as a template in overlapping PCR to generate a full length human HSL ORF with a 3'-His6 tag. This full length insert was cloned into the pFast-BAC vector and the DNA-sequence of several single clones was verified. DNA from a correct full length clone with the 3'His6 tag was used to transform the *E.coli* strain DH10BAC. Resulting bacmid DNA was used to generate a titered baculovirus stock for protein generation. The sequence of the encoded HSL conforms to Swissprot entry Q05469, with the additional C-terminal His6-tag.
2) Protein purification: Culture: 5.5 L, High 5 cells expressing human full length HSL-His[6], 48 hr., containing 25 µM E-64. Cell count: $1.78 \times 10^{10}$ cells/ml, 90% viable.
Cells were thawed. On ice, cells were suspended in Base Buffer containing 10% glycerol, 25 mM Tris-Cl, 300 mM NaCl, 10 mM imidazole, 10 mM 2-mercaptoethanol, 2 µg pepstatin/ml, 2 µg leupeptin/ml, 2 µg antipain/ml, pH 8.0 at 4° C. in a final volume of 475 ml with $3.75 \times 10^7$ cells/ml. Sanitation was done at 3×30 sec., Lubrol PX was added to 0.2% final concentration followed by stirring for 15 min. at 4° C. and centrifugation at 25 k×g, 60 min., 4° C. Soluble proteins were mixed with 60 ml of pre-washed and equilibrated Ni-NTA Agarose (Qiagen 30210) followed by tumbling end-over-end, 45 min., 4° C., centrifugation 1000 rpm 5 min and letting resin settle 5 min. Supernatant was removed, the resin washed in the centrifuge vessel using 5 volumes of Base Buffer containing 0.2% Lubrol PX. Centrifugation was done again, then the supernatant discarded. The resin was poured onto a 0.8 µm membrane in a disposable filter unit (Nalge 450-0080), and washed with 5 volumes of Base Buffer containing 0.2% Lubrol PX. It was then washed with 30 volumes of Base Buffer containing 60 mM imidazole pH 7.5 at 4° C. The protein was eluated with 5 volumes of 25 mM Tris-Cl, 300 mM NaCl, 200 mM imidazole, 10 mM 2-mercaptoethanol, pH 7.5 at 4° C. by tumbling resin with buffer end-over-end, 30 min., 4° C. The resin was captured on a 0.2 µm membrane disposable filter unit (Millipore SCGP U02 RE) and the eluate collected in the reservoir. The eluate was concentrated using a 30 k MWCO centrifugal filter device (Sartorius Vivascience Vivacell 100, VC1022), to 20 ml. It was then dialyzed overnight at 4° C., two times against 2 L of 10% glycerol, 25 mM Tris-Cl, 300 mM NaCl, 0.2 mM EDTA, 0.2 mM DTT, pH 7.5 at 4° C. The protein was filtered using a 0.22 µm disposable filter unit (Millipore SCGP00525). The protein concentration was calculated from absorbance at 280 nm, using 280=0.67 cm-1 mg-1. Yield was 235 mg, total. The protein was stored at −80° C.

Human Hormone-Sensitive Lipase (HSL) Enzyme Inhibition Assay:

HSL enzyme activity was measured by a colorimetric assay using 2,3-dimercapto-1-propanol tributyrate (Aldrich, St. Louis, Mo.) as a substrate. Typically, 1.5 mM 2,3-dimercapto-1-propanol tributyrate (DMPT) in 100 mM MOPS, pH 7.2, 0.2 mg/ml fatty acid-free BSA was prepared by sonication at 4° C. to homogenous suspension. Test compounds (2 mM stock in DMSO) were diluted 3 fold in series in DMSO. Compound solutions were diluted 24 fold in 1.5 mM DMPT containing solution and 18 ul per well was added to 384-well microplates (Corning Costar). Twelve microliters per well of human HSL (15 ug/ml) was added and the reaction mixture was incubated at 37° C. for 20 minutes. Six microliters of 12 mM dithio-bis-(2-nitrobenzoic acid) (DTNB) in DMSO plus 1.2% SDS and 0.6% Triton X-100 were added and the mixture was incubated at room temperature for 15 minutes. Product production was monitored by reading absorbance at 405 nm on an Envision Reader (PerkinElmer Life and Analytical Sciences, Shelton, Conn.).

Cellular Assay:

The following assay was used to measure the effect of the compounds to inhibit lipolysis in intact cells (adipocytes). 3T3-L1 pre-adipocyte cells were plated into 96-well plates at a density of 20,000 cells/well in 200ul growth media (DMEM/10% Calf Serum/1× antibiotic-antimycotic) until confluent. At 48 hours post-confluency, the medium was removed and the cells were differentiated into adipocytes with differentiation medium (DMEM/10% FBS/1× Antibiotic-Antimycotic PLUS: 1 uM IBMX (3-Isobutyl-1-methylxanthine) Inhibitor of phosphodiesterases, 1 uM Dexamethasone, 1 uM Rosiglitazone, 10 ug/ml Insulin). The cells were incubated in said medium for 3 days and then medium was changed to post-differentiation medium (DMEM/10% FBS PLUS: 10 ug/ml Insulin) and the cells were incubated for an additional 3 days. The medium was then changed to maintenance media (DMEM/10% FBS). The cells were fed every 3 days with maintenance media until use. The lipolysis assay may be performed on day 9-14 after the initiation of differentiation in 96 well plates.

The lipolysis assay was performed as follows. The adipocytes were washed 2× with 200 ul Krebs Ringer Bicarbonate Hepes buffer (KRBH)/3% BSA. Test compounds were at 10 mM in DMSO and were initially diluted to 5 mM in DMSO. They were then serially diluted 5-fold in DMSO (5 mM to 320 pM). Each compound was then diluted 200-fold into KRBH/3% BSA (0.5% DMSO final). The resulting solutions range from 25 uM to 1.6 pM final. One hundred fifty ul of the diluted compounds were added to each well (in triplicate) and the cells were preincubated 30 min at 37° C. Forskolin (50 uM final) was added to the wells and the cells were incubated 120 minutes at 37° C. One hundred ul was collected into a new 96-well plate for glycerol analysis. The amount of glycerol produced was determined using a glycerol determination kit (Sigma).

| Examples | HSL hum IC50 (uM) |
| --- | --- |
| 1 | 0.06 |
| 2 | 0.01 |
| 3 | 0.02 |
| 4 | 0.01 |
| 5 | 0.16 |
| 6 | 0.09 |
| 7 | 0.02 |
| 8 | 0.03 |
| 9 | 0.03 |
| 10 | 0.02 |
| 11 | 0.05 |
| 12 | 0.02 |
| 13 | 0.02 |
| 14 | 0.74 |
| 15 | 0.43 |

Compounds of formula (I) and their pharmaceutically acceptable salts or esters thereof as described above have $IC_{50}$ values between 0.0001 uM and 1000 uM, particular compounds have $IC_{50}$ values between 0.001 uM and 500 uM, further particular compounds have $IC_{50}$ values between 0.001 uM and 5 uM. These results have been obtained by using the foregoing HSL enzyme inhibition assay (uM means micro-Molar).

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention, the compounds of formula (I) and their pharmaceutically acceptable salts can be used for the treatment or prophylaxis of diabetes, metabolic syndrome, dyslipidemia, atherosclerosis, obesity, cardiovascular diseases, myocardial dysfunction, inflammation, non-alkoholic fatty liver disease or nonalkoholic steatohepatitis. The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given above can be exceeded when this is shown to be indicated.

The invention is illustrated hereinafter by Examples, which have no limiting character.

In case the preparative examples are obtained as a mixture of enantiomers, the pure enantiomers can be separated by methods described herein or by methods known to the man skilled in the art, such as e.g. chiral chromatography or crystallization.

EXAMPLES

Example 1

(5SR,6RS)-8-Benzyl-6-hydroxy-2-(4-trifluoromethoxy-phenyl)-2,8-diaza-spiro[4.5]decan-1-one

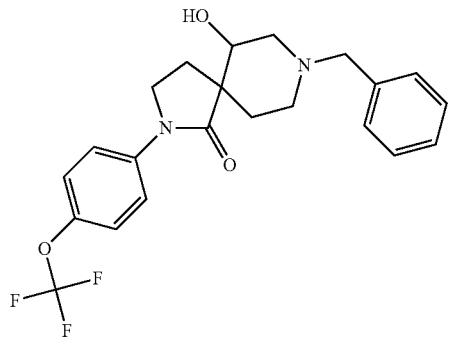 [SMILES: O=C1N(c2ccc(OC(F)(F)F)cc2)CCC12CCN(Cc1ccccc1)CC2O]

Step A: 1-Benzyl-4-(2-methoxy-ethyl)-3-oxo-piperidine-4-carboxylic acid ethyl ester

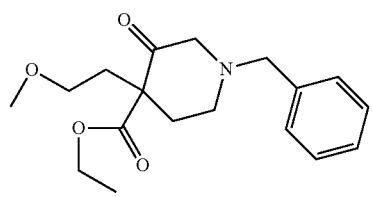 [SMILES: CCOC(=O)C1(CCOC)CCN(Cc2ccccc2)CC1=O]

To a solution of 1-benzyl-3-piperidone-4-carboxylic acid benzyl ester (4.7 g, 18.9 mmol) in dimethylformamide (50 mL) at 0° C. was added potassium tert-butoxide (4.23 g, 37.8 mmol) and the mixture was warmed to room temperature and stirring was continued for 30 minutes. A solution of 1-bromo-2-methoxy-ethane (3.4 mL, 36.0 mmol) in dimethylformamide (10 mL) was added followed by the addition of sodium iodide (1.35 g, 9.0 mmol). The resulting mixture was heated at 80° C. for 2 hours followed by overnight stirring at 50° C. After cooling, the reaction mixture was diluted with diethyl ether (50 mL), washed with water (3×50 mL), brine (50 mL), dried over sodium sulfate and concentrated in vacuo to afford a crude residue which was purified by flash column chromatography (1:9 AcOEt/heptane) to afford the title compound as a light brown oil (2.17g, 38%). MS (ESI): 320.1 (MH+).

Step B: 1-Benzyl-3-hydroxy-4-(2-methoxy-ethyl)-piperidine-4-carboxylic acid ethyl ester

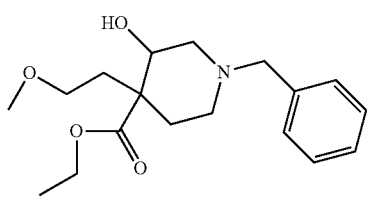 [SMILES: CCOC(=O)C1(CCOC)CCN(Cc2ccccc2)CC1O]

To a solution of 1-benzyl-4-(2-methoxy-ethyl)-3-oxo-piperidine-4-carboxylic acid ethyl ester (774 mg, 2.42 mmol) in MeOH (5 mL) at 0° C. was carefully added sodium borohydride (110 mg, 2.91 mmol) and the reaction mixture was stirred at room temperature for 4 h. The reaction mixture was quenched with 1N NaOH and diluted with further 1N NaOH and ethyl acetate. The organic layer was separated washed with brine, dried ($Na_2SO_4$), filtered and concentrated in vacuo to give a crude residue which was purified by flash column chromatography to give 1-benzyl-3-hydroxy-4-(2-methoxy-ethyl)-piperidine-4-carboxylic acid ethyl ester (610 mg, 78%) as a white solid. MS (ESI): 322.3 (MH+).

The diastereomeric racemates could be subsequently separated by flash column chromatography to give (3RS,4SR)-1-benzyl-3-hydroxy-4-(2-methoxy-ethyl)-piperidine-4-carboxylic acid ethyl ester (298 mg, 38%) MS (ESI): 322.3 (MH+) and (3SR,4SR)-1-benzyl-3-hydroxy-4-(2-methoxy-ethyl)-piperidine-4-carboxylic acid ethyl ester (150 mg, 20%) MS (ESI): 322.3 (MH+).

Step C: (5SR,6RS)-8-Benzyl-6-hydroxy-2-(4-trifluoromethoxy-phenyl)-2,8-diaza-spiro[4.5]decan-1-one

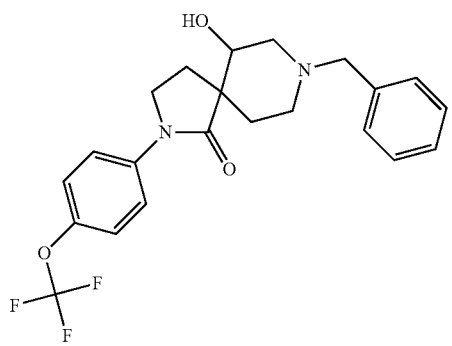 [SMILES: O=C1N(c2ccc(OC(F)(F)F)cc2)CCC12CCN(Cc1ccccc1)CC2O]

To a solution of (3RS,4SR)-1-benzyl-3-hydroxy-4-(2-methoxy-ethyl)-piperidine-4-carboxylic acid ethyl ester (618 mg, 1.92 mmol) and 4-(trifluoromethoxy)aniline (516 µL, 3.85 mmol) in toluene (5 ml) under an argon atmosphere at room temperature, was added dimethylaluminium chloride (0.9M solution in heptane, 4.27 ml, 3.85 mmol) and the mixture was refluxed for 4 hours. The reaction mixture was cooled to room temperature and quenched with sat. $Na_2SO_4$ (aq) solution and the mixture was filtered through Celite® and evaporated under reduced pressure. The crude residue was purified by flash column chromatography (1:1 AcOEt/heptane) to give (5SR,6RS)-8-benzyl-6-hydroxy-2-(4-trifluoromethoxy-phenyl)-2,8-diaza-spiro[4.5]decan-1-one (620 mg, 77%) as a white solid. MS (ESI): 405.4 (MH+).

Example 2

(5RS,6RS)-8-(2-Chloro-benzenesulfonyl)-6-hydroxy-2-(4-trifluoromethoxy-phenyl)-2,8-diaza-spiro[4.5]decan-1-one Step A (5SR,6RS)-6-Hydroxy-2-(4-trifluoromethoxy-phenyl)-2,8-diaza-spiro[4.5]decan-1-one

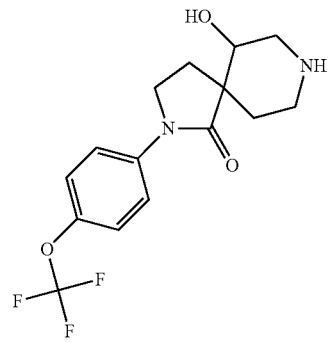 [SMILES: O=C1N(c2ccc(OC(F)(F)F)cc2)CCC12CCNCC2O]

A mixture of (5SR,6RS)-8-benzyl-6-hydroxy-2-(4-trifluoromethoxy-phenyl)-2,8-diaza-spiro[4.5]decan-1-one (293 mg, 0.70 mmol), acetic acid (1 ml) and Pearlman's catalyst (195 mg) in MeOH (20 ml) was stirred at room temperature under an atmospheric pressure of $H_2$ for 4 h. The catalyst was removed by filtration and the filtrate was evaporated to give a crude residue was dissolved in water and the solution was made basic with 1N NaOH and extracted with ethyl acetate. The combined organic extracts were dried ($Na_2SO_4$), filtered and evaporated under reduced pressure to yield (5SR,6RS)-6-hydroxy-2-(4-trifluoromethoxy-phenyl)-2,8-diaza-spiro[4.5]decan-1-one as an off white solid. MS (ESI): 331.2 (MH+).

Step B: (5RS,6RS)-8-(2-Chloro-benzenesulfonyl)-6-hydroxy-2-(4-trifluoromethoxy-phenyl)-2,8-diaza-spiro[4.5]decan-1-one

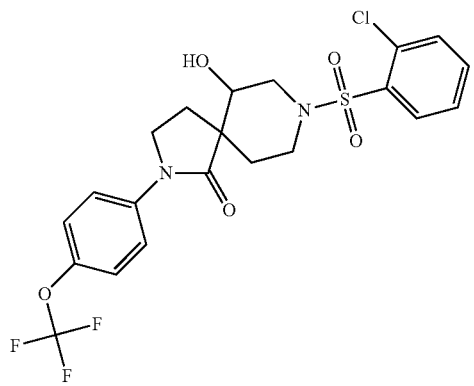 [SMILES: O=C1N(c2ccc(OC(F)(F)F)cc2)CCC12CCN(S(=O)(=O)c1ccccc1Cl)CC2O]

(5SR,6RS)-6-Hydroxy-2-(4-trifluoromethoxy-phenyl)-2,8-diaza-spiro[4.5]decan-1-one (33 mg, 0.10 mmol) was dissolved in pyridine (1 mL) at room temperature and 1,3,5-trimethyl-1H-pyrazole-4-sulfonyl chloride (22 mg, 0.10 mmol) was added and the mixture was stirred overnight at room temperature. The reaction mixture was concentrated in vacuo and the resulting residue was dissolved in AcOEt and washed with 0.1M HCl and brine. The organic layer was dried (Na$_2$SO$_4$), filtered and evaporated under reduced pressure to give a crude residue which was purified by flash column chromatography (4:1 AcOEt/heptane) to yield (5RS,6RS)-8-(2-chloro-benzenesulfonyl)-6-hydroxy-2-(4-trifluoromethoxy-phenyl)-2,8-diaza-spiro[4.5]decan-1-one a colourless solid (36 mg, 71%). MS (ESI): 505.1 (MH+)

Example 3

(5RS,6RS)-8-(2-Chloro-pyridine-3-sulfonyl)-6-hydroxy-2-(4-trifluoromethoxy-phenyl)-2,8-diaza-spiro[4.5]decan-1-one

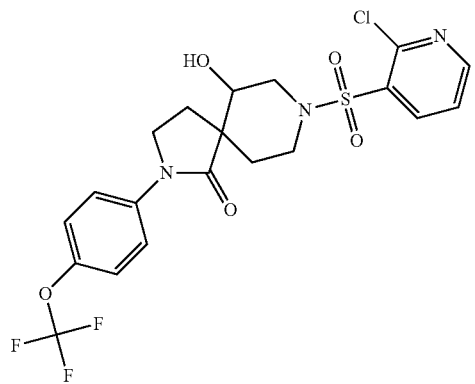 [SMILES: O=C1N(c2ccc(OC(F)(F)F)cc2)CCC12CCN(S(=O)(=O)c1cccnc1Cl)CC2O]

The title compound was prepared in analogy to example 2 step B from a mixture of (5SR,6RS)-6-hydroxy-2-(4-trifluoromethoxy-phenyl)-2,8-diaza-spiro[4.5]decan-1-one (described in example 2 step A) and 2-chloro-pyridine-3-sulfonyl chloride. Colourless solid. MS (ESI): 506.0 (MH$^+$)

Example 4

(5RS,6RS)-6-Hydroxy-8-(2-trifluoromethoxy-benzenesulfonyl)-2-(4-trifluoromethoxy-phenyl)-2,8-diaza-spiro[4.5]decan-1-one

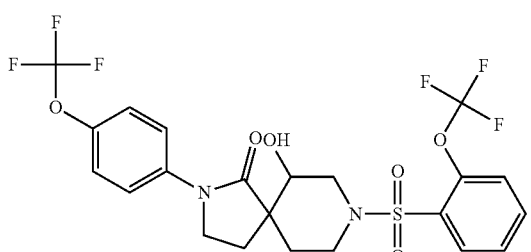

The title compound was prepared in analogy to example 2 step B from a mixture of (5SR,6RS)-6-hydroxy-2-(4-trifluoromethoxy-phenyl)-2,8-diaza-spiro[4.5]decan-1-one (described in example 2 step A) and 2-trifluoromethoxy-benzenesulfonyl chloride. Colourless solid. MS (ESI): 555.2 (MH$^+$)

Example 5

(5RS,6RS)-8-Cyclopropanesulfonyl-6-hydroxy-2-(4-trifluoromethoxy-phenyl)-2,8-diaza-spiro[4.5]decan-1-one

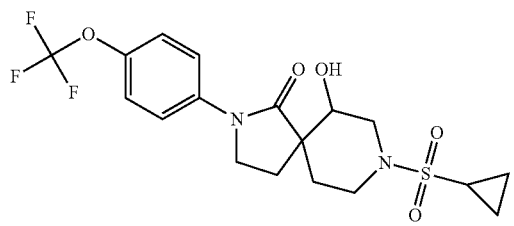 [SMILES: O=C1N(c2ccc(OC(F)(F)F)cc2)CCC12CCN(S(=O)(=O)C1CC1)CC2O]

The title compound was prepared in analogy to example 2 step B from a mixture of (5SR,6RS)-6-hydroxy-2-(4-trifluoromethoxy-phenyl)-2,8-diaza-spiro[4.5]decan-1-one (described in example 2 step A) and cyclopropanesulfonyl chloride. Colourless solid. MS (ESI): 435.3 (MH$^+$)

Example 6

(5RS,6RS)-6-Hydroxy-8-(2-methyl-propane-1-sulfonyl)-2-(4-trifluoromethoxy-phenyl)-2,8-diaza-spiro[4.5]decan-1-one

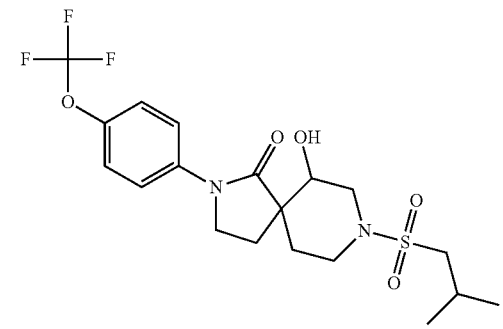 [SMILES: CC(C)CS(=O)(=O)N1CCC2(CCN(c3ccc(OC(F)(F)F)cc3)C2=O)C(O)C1]

The title compound was prepared in analogy to example 2 step B from a mixture of (5SR,6RS)-6-hydroxy-2-(4-trifluoromethoxy-phenyl)-2,8-diaza-spiro[4.5]decan-1-one (described in example 2 step A) and propane-2-sulfonyl chloride. White solid. MS (ESI): 451.2 (MH$^+$)

Example 7

(5RS,6RS)-8-(2-Chloro-benzenesulfonyl)-6-hydroxy-2-[4-(2,2,2-trifluoro-ethyl)-phenyl]-2,8-diaza-spiro[4.5]decan-1-one

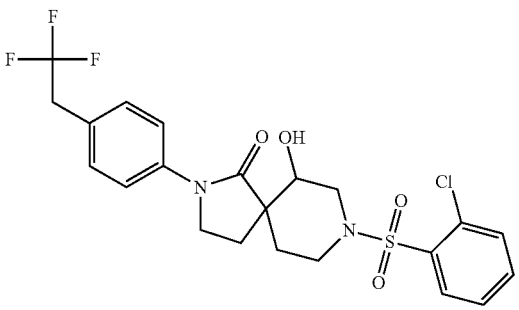 [SMILES: O=C1N(c2ccc(CC(F)(F)F)cc2)CCC12CCN(S(=O)(=O)c1ccccc1Cl)CC2O]

Step A: (5SR,6RS)-8-Benzyl-6-hydroxy-2-[4-(2,2,2-trifluoro-ethyl)-phenyl]-2,8-diaza-spiro[4.5]decan-1-one

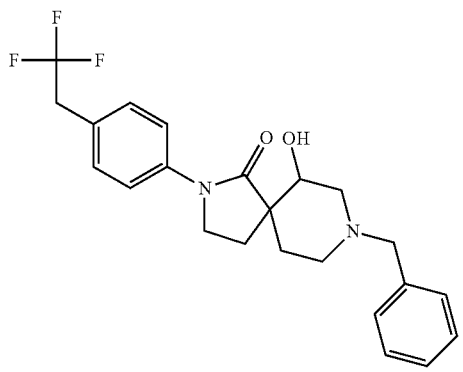 [SMILES: O=C1N(c2ccc(CC(F)(F)F)cc2)CCC12CCN(Cc1ccccc1)CC2O]

The title compound was prepared in analogy to example 1 step C from a mixture of (3RS,4SR)-1-benzyl-3-hydroxy-4-(2-methoxy-ethyl)-piperidine-4-carboxylic acid ethyl ester and 4-(2,2,2-trifluoro-ethyl)-phenylamine). Light yellow solid. MS (ESI): 419.3 (MH$^+$)

Step B: (5SR,6RS)-6-Hydroxy-2-[4-(2,2,2-trifluoro-ethyl)-phenyl]-2,8-diaza-spiro[4.5]decan-1-one

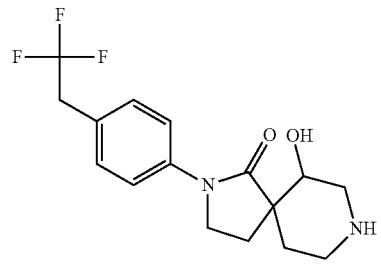 [SMILES: O=C1N(c2ccc(CC(F)(F)F)cc2)CCC12CCNCC2O]

The title compound was prepared in analogy to example 2 step A from a mixture of (5SR,6RS)-8-benzyl-6-hydroxy-2-[4-(2,2,2-trifluoro-ethyl)-phenyl]-2,8-diaza-spiro[4.5]decan-1-one and Pearlman's catalyst under an atmosphere of hydrogen. White solid. MS (ESI): 329.2 (MH$^+$)

Step C: (5RS,6RS)-8-(2-Chloro-benzenesulfonyl)-6-hydroxy-2-[4-(2,2,2-trifluoro-ethyl)-phenyl]-2,8-diaza-spiro[4.5]decan-1-one

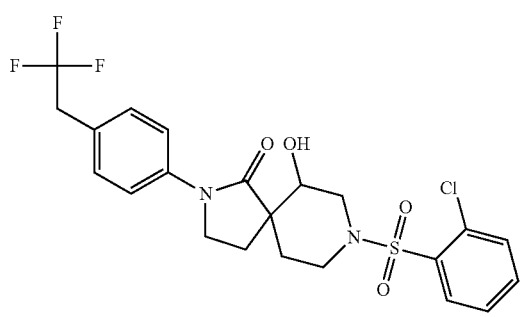 [SMILES: O=C1N(c2ccc(CC(F)(F)F)cc2)CCC12CCN(S(=O)(=O)c1ccccc1Cl)CC2O]

The title compound was prepared in analogy to example 2 step B from a mixture of (5SR,6RS)-6-hydroxy-2-[4-(2,2,2-trifluoro-ethyl)-phenyl]-2,8-diaza-spiro[4.5]decan-1-one (described in example 7 step B) and 2-chloro-benzenesulfonyl chloride. Colourless solid. MS (ESI): 503.0 (MH$^+$)

Example 8

(5RS,6RS)-6-Hydroxy-8-(2-methyl-2H-pyrazole-3-sulfonyl)-2-[4-(2,2,2-trifluoro-ethyl)-phenyl]-2,8-diaza-spiro[4.5]decan-1-one

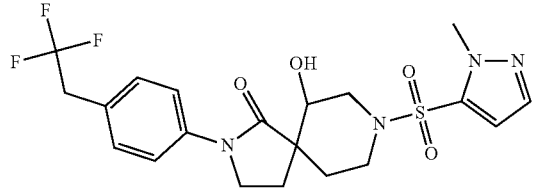 [SMILES: Cn1nccc1S(=O)(=O)N1CCC2(CCN(c3ccc(CC(F)(F)F)cc3)C2=O)C(O)C1]

The title compound was prepared in analogy to example 2 step B from a mixture of (5SR,6RS)-6-hydroxy-2-[4-(2,2,2-trifluoro-ethyl)-phenyl]-2,8-diaza-spiro[4.5]decan-1-one (described in example 7 step B) and 2-methyl-2H-pyrazole-3-sulfonyl chloride. Light yellow solid. MS (ESI): 473.2 (MH$^+$)

Example 9

(5RS,6RS)-8-(2,2-Dimethyl-propane-1-sulfonyl)-6-hydroxy-2-[4-(2,2,2-trifluoro-ethyl)-phenyl]-2,8-diaza-spiro[4.5]decan-1-one

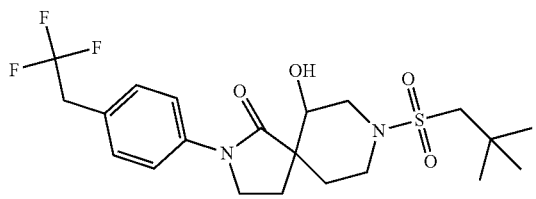 [SMILES: CC(C)(C)CS(=O)(=O)N1CCC2(CCN(c3ccc(CC(F)(F)F)cc3)C2=O)C(O)C1]

The title compound was prepared in analogy to example 2 step B from a mixture of (5SR,6RS)-6-hydroxy-2-[4-(2,2,2-trifluoro-ethyl)-phenyl]-2,8-diaza-spiro[4.5]decan-1-one (described in example 7 step B) and 2,2-dimethyl-propane-1-sulfonyl chloride. Light yellow solid. MS (ESI): 463.2 (MH$^+$)

Example 10

(5RS,6RS)-8-(2-Chloro-benzenesulfonyl)-6-hydroxy-2-[-4-((rac)-2,2,2-trifluoro-1-methyl-ethoxy)-phenyl]-2,8-diaza-spiro[4.5]decan-1-one

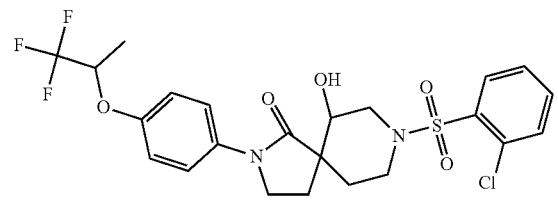 [SMILES: CC(Oc1ccc(N2CCC3(CCN(S(=O)(=O)c4ccccc4Cl)CC3O)C2=O)cc1)C(F)(F)F]

Step A: (5SR,6RS)-8-Benzyl-6-hydroxy-2-[-4-((rac)-2,2,2-trifluoro-1-methyl-ethoxy)-phenyl]-2,8-diaza-spiro[4.5]decan-1-one

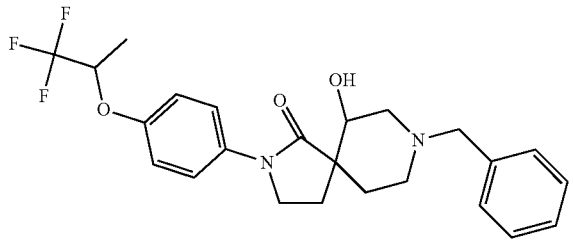 [SMILES: CC(Oc1ccc(N2CCC3(CCN(Cc4ccccc4)CC3O)C2=O)cc1)C(F)(F)F]

The title compound was prepared in analogy to example 1 step C from a mixture of (3RS,4SR)-1-benzyl-3-hydroxy-4-(2-methoxy-ethyl)-piperidine-4-carboxylic acid ethyl ester and (rac)-4-(2,2,2-trifluoro-1-methyl-ethoxy)-phenylamine. Light yellow solid. MS (ESI): 449.2 (MH$^+$)

Preparation of the starting material, (rac)-4-(2,2,2-trifluoro-1-methyl-ethoxy)-phenylamine:

i) To a solution of 1-fluoro-4-nitro-benzene (4.24 g) and (rac)-1,1,1-trifluoro-propan-2-ol(4.563 g) in acetonitil (50 ml) under an argon atmosphere was added at RT Cs$_2$CO$_3$ (13.04 g) and the mixture was refluxed for 10 h. It was then acidified with diluted aqueous HCL10 and partitioned between AcOEt and water. The layers were separated, dried over Na$_2$SO$_4$ and the solvent was then evaporated off to give (rac)-1-nitro-4-(2,2,2-trifluoro-1-methylethoxy)-benzene as brown oil (6.74 g) that was used without further purification.

ii) (rac)-1-nitro-4-(2,2,2-trifluoro-1-methyl-ethoxy)-benzene (6.74 g) in methanol (80 ml) were hydrogenated at RT over Pd/C (10%, 500 mg) under a hydrogen atmosphere (atmospheric pressure) for 12 h. The catalyst was filtered off and filtrate concentrated in vacuo to give the desired (rac)-4-(2,2,2-trifluoro-1-methyl-ethoxy)-phenylamine (5.8 g) as a light yellow oil. MS (ESI): 206.1 (MH$^+$).

Step B: (5SR,6RS)-6-Hydroxy-2-[4-((rac)-2,2,2-trifluoro-1-methyl-ethoxy)-phenyl]-2,8-diaza-spiro[4.5]decan-1-one

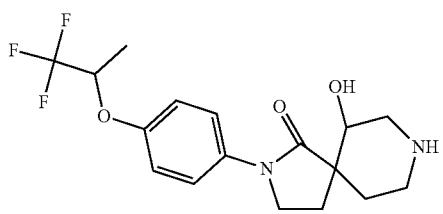 [SMILES: CC(Oc1ccc(N2CCC3(CCNCC3O)C2=O)cc1)C(F)(F)F]

The title compound was prepared in analogy to example 2 step A from a mixture of (5 SR,6RS)-8-benzyl-6-hydroxy-2-[4-((rac)-2,2,2-trifluoro-1-methyl-ethoxy)-phenyl]-2,8-diaza-spiro[4.5]decan-1-one and Pearlman's catalyst under an atmosphere of hydrogen. Light brown solid. MS (ESI): 359.1 (MH$^+$)

Step C: (5RS,6RS)-8-(2-Chloro-benzenesulfonyl)-6-hydroxy-2-[4-((rac)-2,2,2-trifluoro-1-methyl-ethoxy)-phenyl]-2,8-diaza-spiro[4.5]decan-1-one

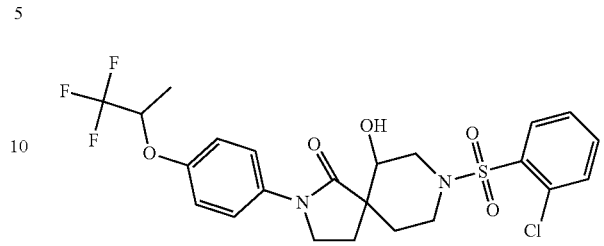

The title compound was prepared in analogy to example 2 step B from a mixture of (5SR,6RS)-6-hydroxy-2-[4-((rac)-2,2,2-trifluoro-1-methyl-ethoxy)-phenyl]-2,8-diaza-spiro [4.5]decan-1-one and 2-chloro-benzenesulfonyl chloride. Light yellow solid. MS (ESI): 533.1 (MH$^+$)

Example 11

(5RS,6RS)-6-Hydroxy-8-(2-methyl-2H-pyrazole-3-sulfonyl)-2-[4-((rac)-2,2,2-trifluoro-1-methyl-ethoxy)-phenyl]-2,8-diaza-spiro[4.5]decan-1-one

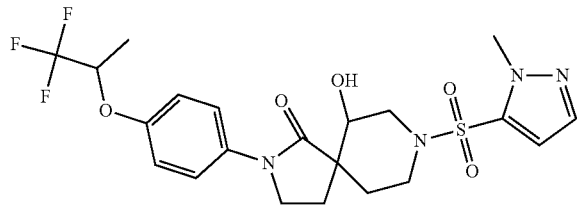 [SMILES: CC(Oc1ccc(N2CCC3(CCN(S(=O)(=O)c4ccnn4C)CC3O)C2=O)cc1)C(F)(F)F]

The title compound was prepared in analogy to example 2 step B from a mixture of (5SR,6RS)-6-hydroxy-2-[4-((rac)-2,2,2-trifluoro-1-methyl-ethoxy)-phenyl]-2,8-diaza-spiro [4.5]decan-1-one (described in example 10 step B) and 2-methyl-2H-pyrazole-3-sulfonyl chloride. Light yellow solid. MS (ESI): 503.1 (MH$^+$)

Example 12 rac-8-(2-Chloro-benzenesulfonyl)-2-(4-trifluoromethoxy-phenyl)-2,8-diaza-spiro[4.5]decane-1,6-dione

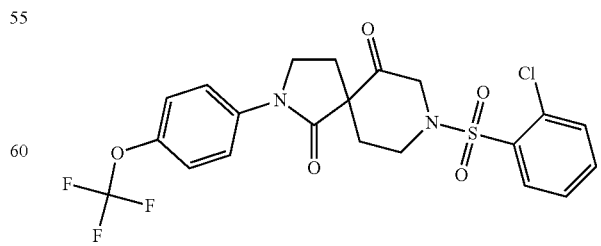

In a 10 mL round-bottomed flask, oxalyl chloride (46.1 mg, 31.8 μl, 356 μmol) was combined with DCM (5 mL) to give a colorless solution. DMSO (27.8 mg, 25.3 μl, 356 μmol) was added drop wise at −78° C. The reaction was stirred for 15 min. A solution of 8-(2-chlorophenylsulfonyl)-6-hydroxy-2-(4-(trifluoromethoxy)phenyl)-2,8-diazaspiro[4.5]decan-1-one (124 mg, 246 μmol) in DCM (1 mL) was added. The reaction mixture was stirred for 30 min at −40° C. Triethylamine (74.6 mg, 103 μl, 737 μmol) was added drop wise and the reaction mixture was heated to r.t. and stirred for 3 h. The reaction mixture was poured into 15 mL DCM and washed with H₂O (2×10 mL).The organic layers were combined, washed with brine, dried over Na₂SO₄ and concentrated in vacuo. The crude residue was purified by flash chromatography (0 to 100% AcOEt in heptane) to afford the title compound as an off-white solid (73 mg, 59%). MS (ESI): 503.1 (MH⁺).

Example 13

(5RS,6RS)-8-(2-Chloro-benzenesulfonyl)-6-hydroxy-6-methyl-2-(4-trifluoromethoxy-phenyl)-2,8-diaza-spiro[4.5]decan-1-one and Example 14: (5RS, 6SR)-8-(2-Chloro-benzenesulfonyl)-6-hydroxy-6-methyl-2-(4-trifluoromethoxy-phenyl)-2,8-diaza-spiro[4.5]decan-1-one

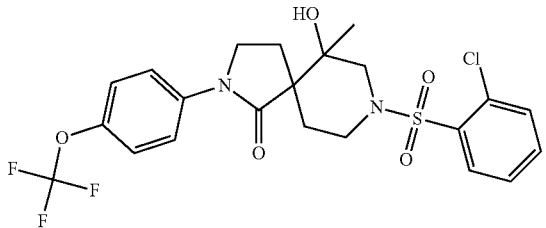 [SMILES: CC1(O)CN(S(=O)(=O)c2ccccc2Cl)CCC12CCN(c1ccc(OC(F)(F)F)cc1)C2=O]

Under argon in a 10 mL round-bottomed flask, cerous(III)-chloride anhydrous (32.3 mg, 131 μmol) was combined with THF (2 ml) to give a white suspension. The suspension was cooled to 0° C. in an ice bath and stirred for 40 min. A solution of rac-8-(2-chloro-benzenesulfonyl)-2-(4-trifluoromethoxy-phenyl)-2,8-diaza-spiro[4.5]decane-1,6-dione (36.6 mg, 72.8 μmol) in THF was added drop wise. Stirring was continued for 35 min followed by the drop wise addition of methylmagnesium iodide (3M solution in diethyl ether, 43.7 μl, 131 μmol). The reaction mixture was stirred over night from 0° C. to r.t. The reaction mixture was poured into ice/H₂O and saturated NH₄Cl solution was added and extracted with EtOAc (3×20 mL).The organic layers were combined and washed with sat NaCl combined and dried over Na₂SO₄ and concentrated in vacuo. The crude residue was purified by flash column chromatography (EtOAc/MeOH/H₂O 93:5:2) to give (5RS,6R5)-8-(2-chloro-benzenesulfonyl)-6-hydroxy-6-methyl-2-(4-trifluoromethoxy-phenyl)-2,8-diaza-spiro [4.5]decan-1-one (9.6 mg, 25%) as a light yellow solid MS (ESI): 519.2 (MH⁺) and (5RS,6SR)-8-(2-chloro-benzenesulfonyl)-6-hydroxy-6-methyl-2-(4-trifluoromethoxy-phenyl)-2,8-diaza-spiro[4.5]decan-1-one (7.4 mg, 20%) as a light yellow solid MS (ESI): 519.2 (MH⁺).

Example 15

(5RS,6SR)-8-(2-Chloro-benzenesulfonyl)-6-hydroxy-2-(4-trifluoromethoxy-phenyl)-2,8-diaza-spiro [4.5]decan-1-one

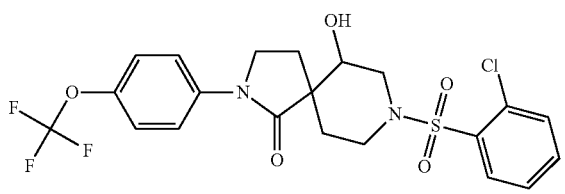 [SMILES: O=C1N(c2ccc(OC(F)(F)F)cc2)CCC12CCN(S(=O)(=O)c1ccccc1Cl)CC2O]

To a solution of rac-8-(2-chloro-benzenesulfonyl)-2-(4-trifluoromethoxy-phenyl)-2,8-diaza-spiro[4.5]decane-1,6-dione (34 mg, 67.6 μmol) in methanol was added sodium borohydride (2.81 mg, 74.4 μmol). The reaction mixture was stirred at room temperature for 6 h. The reaction mixture was quenched with 1N NaOH and diluted with further 1N NaOH and ethyl acetate. The organic layer was separated washed with brine, dried (Na₂SO₄), filtered and concentrated in vacuo to give a crude residue which was purified by flash column chromatography to give the title compound as an off white solid (5 mg, 15%) MS (ESI): 505.1 (MH⁺)

Example A

A compound of formula (I) can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:

1. A compound of formula (I),

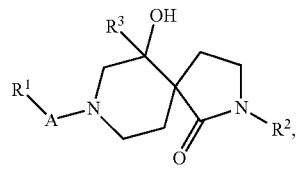

wherein

R¹ is selected from the group consisting of alkyl, cycloalkyl, haloalkyl, pyrazolyl, phenyl, and pyridinyl wherein said pyrazolyl, phenyl and pyfidinyl are optionally substituted with one to three substituents independently selected from the group conststing of alkyl, cycloalkyl, cycloalkylalkyl, halogen, haloalkyl, hydroxyl, hydroxyalkyl, alkoxy, alkoxyalkyl and hydroxyhaloalkyl;

R² is phenyl substituted with one to three substituents independently selected from haloalkyl and haloalkoxy;
R³ is hydrogen or alkyl;
A is —S(O)₂—; and
or a pharmaceutically acceptable salt thereof.

2. A compound according to claim 1, wherein R¹ is selected from the group consisting of alkyl, cycloalkyl, haloalkyl, phenyl, substituted pyrazolyl, substituted phenyl and substituted pyridinyl, wherein said substituted pyrazolyl, substituted phenyl and substituted pyridinyl are substituted with one to three substituents independently selected from the group consisting of alkyl, halogen and haloalkoxy.

3. A compound according to claim 1, wherein R¹ is selected from the group consisting of: alkyl, pyrazolyl substituted with one alkyl and phenyl substituted with one halogen.

4. A compound according to claim 1, selected from the group consisting of:
- (5RS,6RS)-8-(2-Chloro-benzenesulfonyl)-6-hydroxy-2-(4-trifluoromethoxy-phenyl)-2,8-diaza-spiro[4.5]decan-1-one;
- (5RS,6RS)-8-(2-Chloro-pyridine-3-sulfonyl)-6-hydroxy-2-(4-trifluoromethoxy-phenyl)-2,8-diaza-spiro[4.5]decan-1-one;
- (5RS,6RS)-6-Hydroxy-8-(2-trifluoromethoxy-benzenesulfonyl)-2-(4-trifluoromethoxy-phenyl)-2,8-diaza-spiro[4.5]decan-1-one;
- (5RS,6RS)-8-Cyclopropanesulfonyl-6-hydroxy-2-(4-trifluoromethoxy-phenyl)-2,8-diaza-spiro[4.5]decan-1-one;
- (5RS,6RS)-6-Hydroxy-8-(2-methyl-propane-1-sulfonyl)-2-(4-trifluoromethoxy-phenyl)-2,8-diaza-spiro[4.5]decan-1-one;
- (5RS,6RS)-8-(2-Chloro-benzenesulfonyl)-6-hydroxy-2-[4-(2,2,2-trifluoro-ethyl)-phenyl]-2,8-diaza-spiro[4.5]decan-1-one;
- (5RS,6RS)-6-Hydroxy-8-(2-methyl-2H-pyrazole-3-sulfonyl)-2-[4-(2,2,2-trifluoro-ethyl)-phenyl]-2,8-diaza-spiro[4.5]decan-1-one;
- (5RS,6RS)-8-(2,2-Dimethyl-propane-1-sulfonyl)-6-hydroxy-2-[4-(2,2,2-trifluoro-ethyl)-phenyl]-2,8-diaza-spiro[4.5]decan-1-one;
- (5RS,6RS)-8-(2-Chloro-benzenesulfonyl)-6-hydroxy-2-[4-((rac)-2,2,2-trifluoro-1-methyl-ethoxy)-phenyl]-2,8-diaza-spiro[4.5]decan-1-one;
- (5RS,6RS)-6-Hydroxy-8-(2-methyl-2H-pyrazole-3-sulfonyl)-2-[4-((rac)-2,2,2-trifluoro-1-methyl-ethoxy)-phenyl]-2,8-diaza-spiro[4.5]decan-1-one;
- (5RS,6RS)-8-(2-Chloro-benzenesulfonyl)-6-hydroxy-6-methyl-2-(4-trifluoromethoxy-phenyl)-2,8-diaza-spiro[4.5]decan-1-one;
- (5RS,6SR)-8-(2-Chloro-benzenesulfonyl)-6-hydroxy-6-methyl-2-(4-trifluoromethoxy-phenyl)-2,8-diaza-spiro[4.5]decan-1-one; and
- (5RS,6SR)-8-(2-Chloro-benzenesulfonyl)-6-hydroxy-2-(4-trifluoromethoxy-phenyl)-2,8-diaza-spiro[4.5]decan-1-one.

5. A compound according to claim 1, selected from the group consisting of:
- (5RS,6RS)-8-(2-Chloro-benzenesulfonyl)-6-hydroxy-2-[4-(2,2,2-trifluoro-ethyl)-phenyl]-2,8-diaza-spiro[4.5]decan-1-one;
- (5RS,6RS)-6-Hydroxy-8-(2-methyl-2H-pyrazole-3-sulfonyl)-2-[4-(2,2,2-trifluoro-ethyl)-phenyl]-2,8-diaza-spiro[4.5]decan-1-one;
- (5RS,6RS)-8-(2,2-Dimethyl-propane-1-sulfonyl)-6-hydroxy-2-[4-(2,2,2-trifluoro-ethyl)-phenyl]-2,8-diaza-spiro[4.5]decan-1-one; and
- (5RS,6RS)-6-Hydroxy-8-(2-methyl-2H-pyrazole-3-sulfonyl)-2-[4-((rac)-2,2,2-trifluoro-1-methyl-ethoxy)-phenyl]-2,8-diaza-spiro[4.5]decan-1-one.

6. A pharmaceutical composition comprising a compound according to claim 1 and a therapeutically inert carrier.

\* \* \* \* \*